United States Patent
Zink et al.

(10) Patent No.: US 9,918,463 B2
(45) Date of Patent: Mar. 20, 2018

(54) BIOREACTOR

(75) Inventors: Roger Zink, Widensolen (FR);
Hermann Rees, Merzhausen (DE);
Ottmar Heiny, Reute (DE)

(73) Assignee: BIOSTAGE, INC., Holliston, MA (US)

( * ) Notice: Subject to any disclaimer, the term of this patent is extended or adjusted under 35 U.S.C. 154(b) by 651 days.

(21) Appl. No.: 14/130,953

(22) PCT Filed: May 23, 2012

(86) PCT No.: PCT/EP2012/059560
§ 371 (c)(1),
(2), (4) Date: Aug. 22, 2014

(87) PCT Pub. No.: WO2013/004431
PCT Pub. Date: Jan. 13, 2013

(65) Prior Publication Data
US 2014/0377848 A1    Dec. 25, 2014

(30) Foreign Application Priority Data
Jul. 7, 2011 (DE) .......................... 10 2011 107 400

(51) Int. Cl.
C12M 3/00 (2006.01)
C12M 1/00 (2006.01)
(Continued)

(52) U.S. Cl.
CPC ........... A01N 1/0247 (2013.01); C12M 21/08 (2013.01); C12M 25/14 (2013.01); C12M 27/10 (2013.01); C12M 29/12 (2013.01)

(58) Field of Classification Search
CPC .............................. C12M 21/08; A01N 1/0242
See application file for complete search history.

(56) References Cited

U.S. PATENT DOCUMENTS 4,310,437 A * 1/1982 Schreiber ............... B01D 19/02
                                                     209/169
5,248,613 A * 9/1993 Roubicek ............. B01J 19/1875
                                                     210/219
(Continued)

OTHER PUBLICATIONS

Biomaterials, Elsevier Leading Opinion, "A double-chamber rotating bioreactor for the development of tissue-engineered hollow organs: From concept to clinical trial", 10 pages—Biomaterials 30 (2009) pp. 5260-6269, Jul. 18, 2009.

*Primary Examiner* — Nathan A Bowers
(74) *Attorney, Agent, or Firm* — Young Basile Hanlon & MacFarlane, P.C.

(57) ABSTRACT

The invention relates to a bioreactor for charging the outside and the interior of a hollow element (1) or hollow element framework with a liquid, having a housing (2) accommodating the liquid, forming a liquid surface, and a rotation device (3) arranged within the housing (2) and receiving the hollow element (1), which rotation device (3) is for rotating the hollow element (1) about the longitudinal axis (4) thereof in the region of the liquid surface. In known bioreactors of this type, the interior of the hollow element must be flushed with a special device, and so here also a liquid exchange takes place. The object of forming a bioreactor for charging the interior and the outside of hollow elements in such a manner that simplest and cheapest flushing of the interior of the hollow element is ensured is achieved in that the rotation device (3) comprises a scooping chamber (5) running at least in part tangentially to the longitudinal axis, and which is connected via a flow channel (6) to the interior of the hollow element (1).

10 Claims, 1 Drawing Sheet

(51) Int. Cl.
   *A01N 1/00*   (2006.01)
   *A01N 1/02*   (2006.01)
   *C12M 1/12*   (2006.01)
   *C12M 3/04*   (2006.01)

(56) References Cited

U.S. PATENT DOCUMENTS

| | | | | |
|---|---|---|---|---|
| 5,846,498 | A * | 12/1998 | Kingsley | B01J 8/22 261/153 |
| 6,241,381 | B1 * | 6/2001 | Noda | B01F 7/00591 366/262 |
| 2003/0199083 | A1 * | 10/2003 | Vilendrer | C12M 21/08 435/297.2 |
| 2004/0219659 | A1 * | 11/2004 | Altman | C12M 21/08 435/284.1 |
| 2011/0033918 | A1 * | 2/2011 | Asnaghi | C12M 21/08 435/289.1 |

* cited by examiner

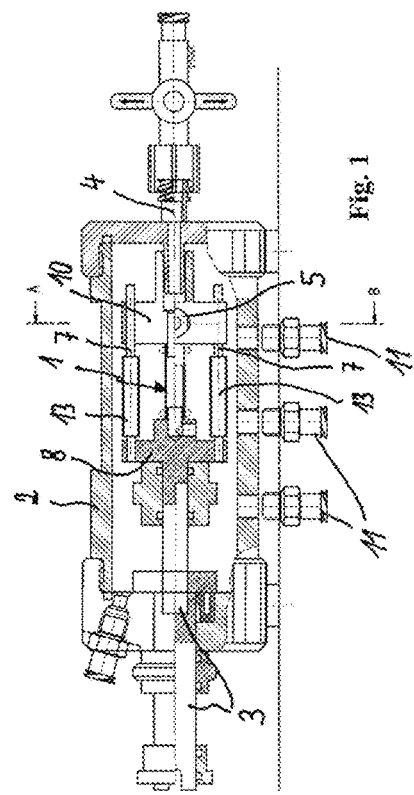
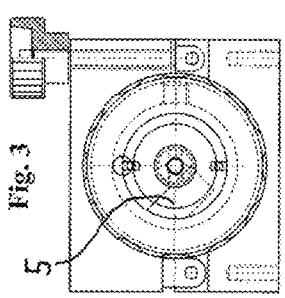
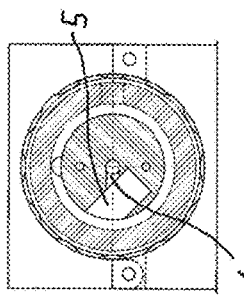

BIOREACTOR

BACKGROUND

Field of the Invention

The invention relates to a bioreactor.

Discussion

Bioreactors for acting with a liquid upon the outside and interior of hollow organs are known from the prior art, for example the specialist article by M. A. Asnaghi et al "A double-chamber rotation bioreactor for the development of tissue-engineered hollow organs: From concept to clinical trial" from Biomaterials 30, 2009, 5260-9, 1-10. The need to act with a liquid upon hollow organs in this way arises particularly in the context of transplantation medicine and regenerative medicine in which people having an incurably diseased organ are implanted either with artificial replacement organs or with donor organs. In both instances, the artificial replacement organs (scaffolds) or the donor organs have to be colonized by the patient's stem cells which are differentiated by the addition of chemicals and specific growth factors. This action upon the organs or scaffolds with stem cells is necessary in order to ensure the functionality of the organ and to prevent contamination with other cells, bacteria or fungi and therefore also minimize rejection reactions. If the replacement organ is the donor organ from another person, this also has to be freed of any cells of the donor person before treatment with the stem cells of the recipient. Bioreactors serve these purposes. If the organs or replacement organs are hollow organs, such as windpipes, bronchi, blood vessels, ureters, etc., special bioreactors are used which enable both the outside of the organ and the interior to be acted upon with a liquid. A special bioreactor of this type is described in the abovementioned article. The liquid with which the hollow organ is acted upon may contain chemicals to destroy cells which are still present and, in the recolonization of the organ with the stem cells of the organ recipient, is composed of a cell suspension.

In known bioreactors for supplying hollow organs with a liquid, in particular with a cell suspension, there is the problem that the interior of the hollow organ has to be flushed especially well because liquid exchange also does not take place here due to the movement of the hollow organ within the liquid. This special flushing of the interior is carried out by means of an additional electric or hydraulic pump. The object, therefore, is to develop a bioreactor for acting upon the interior and the outside of hollow organs such as to ensure that the interior of the hollow organ is flushed as simply and as cost-effectively as possible.

This object is achieved by means of the characterizing features of claim 1. Advantageous refinements may be gathered from the subclaims.

SUMMARY

A bioreactor comprising that includes a housing configured to contain a liquid so as to form a liquid level and: a rotary device that is arranged in the housing and is configured for rotating a hollow organ or organ scaffold about a longitudinal axis in a region of the liquid level. The hollow organ or organ scaffold has an exterior exposed to the liquid contained in the housing and an interior in which the rotary device comprises at least one rotatable member for rotatably holding the hollow organ or organ scaffold. The rotatable holding member has a body, a scoop chamber defined in the body of the rotatable holding member and a fluid duct defined in the body of the rotatable holding member the scoop chamber fluidically connected to the interior of the hollow organ or organ scaffold via a flow duct, such that, upon rotation of the rotary device a portion of the liquid contained in the housing enters the scoop chamber and passes through the flow duct to the interior of the hollow organ or organ scaffold, wherein the scoop chamber extends beyond the longitudinal axis defined by the hollow organ or the organ scaffold, and wherein the flow duct branches off laterally from the scoop chamber, wherein the axis of rotation is parallel to the liquid level.

BRIEF DESCRIPTION OF THE DRAWING

The invention is explained in more detail below with reference to the accompanying drawings in which:

FIG. 1 is a cross section through a bioreactor according to an embodiment of the invention as disclosed herein;

FIG. 2 is a section along the line A-A from FIG. 1; and

FIG. 3 shows a side view of the bioreactor from FIG. 3.

DETAILED DESCRIPTION

The bioreactor, illustrated in cross section in FIG. 1, has a cylindrical housing 2 which along its longitudinal axis accommodates a rotary device 3. This rotary device 3 is fastened rotatably in the housing 2 by means of bearings and seals, not illustrated in detail. The housing 2 has on its side ports 11 and a window 12 for a camera, monitoring of the cell suspension by means of suitable biochemical measures being possible through the ports 11, and the entire bioreaction process being capable of being monitored and recorded by means of an external camera through the window 12, and in this case an infrared camera may also be used here in order to monitor the temperature and monitor the colonization of the cells on the hollow organ 1.

The rotary device 3 inside the bioreactor has two holding devices 8 and 10, between which the hollow organ 1 or replacement organ to be treated is suitably mounted. For example, the hollow organ 1 is pushed over corresponding tubular ends of the holding devices 8 and 10 and is fixed there in a way known per se, as illustrated in FIG. 1.

The first holding device 8 is connected to the second holding device 10 via two agitator bars 7 which run parallel to the longitudinal axis of the hollow organ 1 and therefore also of the entire device. In the exemplary embodiment illustrated, the two agitator bars 7 serve, on the one hand, for transmitting the rotation from the first holding device 8 to the second holding device 10. Furthermore, the agitator bars 7 serve for agitating the liquid, in particular the cell suspension, inside the housing 2 and thus preventing cells from clumping together or accumulating on the bottom of the housing 2.

The second holding device 10 has a scoop chamber which is illustrated especially clearly in FIG. 2. This scoop chamber 5 runs tangentially to the longitudinal axis 4 of the mounted hollow organ 1 and consequently to the axis of rotation of the rotary device 3. The scoop chamber 5 is open on one side and is closed on the other side, that is to say, forms a blind hole. The end of this blind hole, as seen along the longitudinal axis of this scoop chamber 5, extends beyond the longitudinal axis 4 of the mounted hollow organ 1. Furthermore, the scoop chamber 5 is connected via a flow duct 6 of smaller diameter to the interior of the hollow organ 1, Specifically in such a way that this flow duct 6 branches off laterally from the scoop chamber 5 and ends in the axis of rotation or in the longitudinal axis 4 of the hollow organ 1. Since the rotary device 3 and the holding device 10 are connected on the inside to the hollow organ, there is a continuous connection from the inlet of the scoop chamber 5 via the flow duct 6 and the interior of the second holding device 10 into the interior of the hollow organ 1 and subsequently, via the interior of the first holding device 8 and three outflow ducts 9 leading this back into the vertically outward from inside of the housing 2. The bioreactor described operates as follows.

First, a cover which, if appropriate, is seated on the housing 2 is removed, and subsequently the rotary device 3 is extracted from the housing 2. The hollow organ 1 or replacement organ to be treated is then mounted between the first holding device 8 and the second holding device 10 of the rotary device 3, this taking place in a way known per se and described above. The aim is to have a reasonably liquid-tight connection between the ends of the hollow organ 1 and the first holding device 8 or second holding device 10. The rotary device 3 having the hollow organ 1 is subsequently inserted into the housing 2 again, and the housing 2 is filled with liquid, for example a cell suspension, up to the height of the axis of rotation.

After the correct chemical parameters and the correct temperature have been reached, the rotary device 3 is set in motion, for example in that the shaft part projecting beyond the housing 2 on the left in the drawing is driven. The first holding device 8 also consequently rotates, and the second holding device 10 is also driven in rotation via the agitator bars 7.

Since the housing 2 is filled about halfway with liquid (cell suspension), whenever the outer orifice of the scoop chamber 5 is below the liquid level as a result of the rotation of the second holding device 10 the scoop chamber 5 dips into the liquid and takes up this liquid particularly during the phase of emergence. As soon as the scoop chamber is located above the liquid level and rotates further, the liquid passes into the flow duct 6 which connects the scoop chamber 5 to the interior of the second holding device 10 and consequently to the interior of the hollow organ 1. The liquid then flows out into the interior of the housing 2 again via the first holding device 8 and the outflow ducts 9. As soon as the orifice of the scoop chamber 5 is at the top, there is no further flow of liquid through the hollow organ 1. Only in the next cycle, that is to say when the orifice of the scoop chamber 5 next emerges from the liquid level, does a flow of liquid through the interior of the hollow organ 1 take place again. However, this intermittent supply has proved sufficient to supply the interior of the hollow organ 1 constantly with fresh liquid and new cells.

In other embodiments, the housing may also have other forms, for example box-shaped or trough-shaped forms. Furthermore, the liquid level may assume other heights, in so far as this is desirable in an individual case, for example if the outside of the hollow organ is not or not to so great an extent to be wetted with the liquid or else is to be wetted permanently with the liquid.

The housing 2 also has a special transport cover not illustrated in the drawing for the purpose of transporting the entire bioreactor to the operating theater. This transport cover is removable and sterilizable and can be attached in a leaktight manner and serves for preserving the sterility of the interior of the housing 2 in a nonsterile environment. Moreover, another cover may be attached for normal operation and then simply lies on the housing 2 and allows gas exchange with the environment, as a result of which an optimal concentration of oxygen and carbon dioxide and therefore a correspondingly optimal partial pressure of these gases in the liquid are maintained inside the housing 2.

Moreover, it is possible to improve the agitation of the cells within the suspension through the use of agitators inside the housing 2. These agitators may take the form of paddles 13 which are attached to the agitator bars 7 and/or to the rotating part, for example to the first holding device 8 or to the second holding device 10. The paddles in this case act as agitator shovels which run as near as possible past the bottom of the bioreactor housing and give rise there to a vortex which loosens cells which have possibly settled.

Finally, it is possible to adapt the bioreactor according to the invention to various matrices. For example the bioreactor may be built for the trachea od children, young people or adults. Adaptation to the various forms of the scaffolds then takes place via corresponding inserts, and in this case, for example, a Y-form for a trachea with two bronchi, or an L-form for a trachea with one bronchus may be used. These inserts also have different diameters, just like the natural organs. The scaffolds are tied to the support by means of surgical silk thread. The hollow organ 1 may also be fastened to the holding devices 8 and 10 in the same way.

The invention claimed is:

1. A bioreactor comprising:
a housing configured to contain a liquid so as to form a liquid level
a rotary device, arranged in the housing and configured for rotating a hollow organ or organ scaffold about a longitudinal axis in a region of the liquid level, the hollow organ or organ scaffold having an exterior exposed to the liquid contained in the housing and an interior, wherein the rotary device comprises at least one rotatable member for rotatably holding the hollow organ or organ scaffold, the rotatable holding member having a body, a scoop chamber defined in the body of the rotatable holding member and a fluid duct defined in the body of the rotatable holding member the scoop chamber fluidically connected to the interior of the hollow organ or organ scaffold via a flow duct, such that, upon rotation of the rotary device a portion of the liquid contained in the housing enters the scoop chamber and passes through the flow duct to the interior of the hollow organ or organ scaffold, wherein the scoop chamber extends beyond the longitudinal axis defined by the hollow organ or the organ scaffold, and wherein the flow duct branches off laterally from the scoop chamber, wherein the axis of rotation is parallel to the liquid level.

2. The bioreactor of claim 1, wherein the rotary device comprises at least one agitator bar, arranged parallel to the longitudinal axis, for agitating the liquid.

3. The bioreactor of claim 1, wherein the rotary device comprises a first holding device configured for holding a first end of the hollow organ or organ scaffold and having at least one outflow duct for connecting the interior of the hollow organ to liquid contained in the housing.

4. The bioreactor of claim 3, wherein the rotary device comprises a second holding device configured for holding a second end of the hollow organ or organ scaffold.

5. The bioreactor of claim 4, wherein the second holding device is connected to the first holding device such that the first holding device is rotatable by a drive of the second holding device.

6. The bioreactor of claim 5, wherein the second holding device is connected to the first holding device via at least one agitator bar, arranged parallel to the longitudinal axis, for agitating the liquid.

7. The bioreactor of claim 2, wherein the rotary device comprises laterally projecting paddles for agitating the liquid.

8. The bioreactor of claim 5, wherein the paddles are arranged on the at least one agitator bar.

9. The bioreactor of claim 1, wherein the housing comprises a sterilizable and removable cover configured to be closed in a leak tight manner.

10. The bioreactor of claim 1, further comprising measuring probes or lateral windows for a camera for monitoring the organ or organ scaffold.

* * * * *